United States Patent
Chen et al.

(10) Patent No.: US 9,639,926 B1
(45) Date of Patent: May 2, 2017

(54) IMAGE PROCESSING TOOL FOR AUTOMATIC FEATURE RECOGNITION AND QUANTIFICATION

(71) Applicants: Xing Chen, Plainfield, IL (US); Ryan J. Stoddard, Seattle, WA (US)

(72) Inventors: Xing Chen, Plainfield, IL (US); Ryan J. Stoddard, Seattle, WA (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 15/263,626

(22) Filed: Sep. 13, 2016

Related U.S. Application Data

(63) Continuation of application No. 14/705,209, filed on May 6, 2015, now abandoned, which is a continuation-in-part of application No. 14/665,932, filed on Mar. 23, 2015, now abandoned.

(51) Int. Cl.
*G06K 9/00* (2006.01)
*G06T 7/00* (2017.01)

(52) U.S. Cl.
CPC .......... *G06T 7/0004* (2013.01); *G06T 7/0095* (2013.01); *G06T 2207/10061* (2013.01); *G06T 2207/30124* (2013.01)

(58) Field of Classification Search
CPC ............................ G06T 7/0004; G06T 7/0095
See application file for complete search history.

(56) References Cited

U.S. PATENT DOCUMENTS

| | | | |
|---|---|---|---|
| 5,130,434 A | 7/1992 | Hagen et al. | |
| 6,130,434 A * | 10/2000 | Mitchell | G01N 23/2204 250/310 |
| 2010/0021682 A1* | 1/2010 | Liang | D03D 15/0011 428/103 |
| 2014/0063244 A1* | 3/2014 | Saha | G05D 1/0246 348/148 |

OTHER PUBLICATIONS

Xu et al, "Determining Fiber Orientation Distribution in Nonwovens with Hough Transform Techniques," 1997, Textile Res. J. 67(8), pp. 563-571.*
Rakesh et al, "Thresholding In Edge Detection: A Statistical Approach," 2004, IEEE Transactions on Image Processing, vol. 13, pp. 927-936.*
John Canny, A Computational Approach to Edge Detection, IEEE Transactions on Pattern Analysis and Machine Intelligence, Nov. 1986, 8(6), IEEE Computer Society, USA, pp. 679-698.
Rishi R. Rakesh et al., Thresholding in Edge Detection: A Statistical Approach, IEEE Transactions on Image Processing, Jul. 2004, 13(7), IEEE Signal Processing Society, USA, pp. 927-936.
(Continued)

*Primary Examiner* — David F Dunphy
(74) *Attorney, Agent, or Firm* — Cherskov Flaynik & Gurda, LLC

(57) ABSTRACT

A system for defining structures within an image is described. The system includes reading of an input file, preprocessing the input file while preserving metadata such as scale information and then detecting features of the input file. In one version the detection first uses an edge detector followed by identification of features using a Hough transform. The output of the process is identified elements within the image.

12 Claims, 8 Drawing Sheets

(56) References Cited

OTHER PUBLICATIONS

Xing Chen, et al., "Fabrication, Formation Mechanism, and Magnetic Properties of Metal Oxide Nanotubes via Electrospinning and Thermal Treatment," J. Phys. Chem C 2011, 115, pp. 373-378.
Jonwan Lee, et al., "Fabrication of Patterned Nanofibrous Mats Using Direct-Write Electrospinning," ACS Publications, Apr. 28, 2012, 2012 American Chemical Society, pp. 7267-7275.
Xu et al., "Determining Fiber Orientation Distribution in Nonwovens with Hough Transform Techniques," 1997, Textile Res. J. 67(8), pp. 563-571.

* cited by examiner

Figure 7A-F

IMAGE PROCESSING TOOL FOR AUTOMATIC FEATURE RECOGNITION AND QUANTIFICATION

CROSS REFERENCE TO RELATED APPLICATIONS

This application claims the benefit as a Continuation of U.S. Utility application Ser. No. 14/705,209 filed on May 6, 2015, presently abandoned, 2015, presently abandoned, the contents of which are hereby incorporated by reference.

CONTRACTUAL ORIGIN OF THE INVENTION

The U.S. Government has rights in this invention pursuant to Contract No. DE-AC02-06CH11357 between the U.S. Department of Energy and UChicago Argonne, LLC, representing Argonne National Laboratory.

BACKGROUND OF THE INVENTION

1. Field of the Invention

The field of the invention is materials testing and image detection, specifically the automatic processing of images of structures such as nanofibers.

2. Background of the Invention

In various embodiments, the invention allows for automated image processing facilitates detection and verification of structures within an image.

In one embodiment, the invention is used in conjunction with images of nanofibers. Nanofiber containing materials have many applications, including in the medical, sports, engineering, and scientific fields. Such materials comprise fibers having diameters less than 100 nanometers. By comparison, a human hair has a diameter of 100 micrometers or 100,000 nanometers.

Given the precise nature of the materials and the manufacturing methods that result in nanofibers, it is important to test nanofibers for quality. A particular application may require very specific characteristics of the nanofiber assembly, such as distance between individual nanofibers and nanofiber diameter. A typical quality test method involves examining the nanofiber under a Scanning Electron Microscope (SEM). Under current approaches, the microscope view is photographed and the sample is analyzed to confirm the diameters of the fibers, and that the fibers are arranged in the desired configuration.

A need exists in the art for a system and method of measuring objective features of a nanofiber material using automated, or semi-automated methods. A single quality control test typically involves hundreds of images, each image in turn containing from ten to several dozen individual fibers. Manual counting and measuring of the fibers is both costly and time-consuming. As described below, in one embodiment, the system includes analytical steps that detect features in the fibers, such as beads, curvatures, and differences in density.

SUMMARY OF INVENTION

An object of the invention is to automatically detect fibers in a SEM photograph of a material. A feature of the invention is that it includes preparatory steps to optimize identification of fibers. An advantage of the invention is that it accepts many types of SEM inputs for processing.

Another object of the invention is to eliminate unnecessary information in the SEM photograph. A feature of the invention is that prior to substantive analysis, scale bar and other secondary information is removed from the photograph. An advantage of the invention is that it does not have to analyze non-fiber image regions.

Yet another objection of the invention is that it accepts color images with various intensity values. A feature of the invention is that color images are pre-processed so as to be acceptable to the system. An advantage of the system is that it accepts many different types of input, including color renderings.

A further object of the invention is to effectively detect edges within the provided image. A feature of the invention is that it implements several edge detection techniques, selecting ones to be optimal for given image type. An advantage of the system is that it can process many different types of input images, often without intervention.

Another object of the invention is to identify fibers from the edge detection information. A feature of the invention is that it uses a Hough transform to identify the most promising edges as the likely nanofiber edges. A benefit of the invention is that it identifies fibers on the basis of the edge detection with efficiency and high-level of accuracy.

An additional object of the invention is to identify fibers from the edge detection information of real-life images that are not ideal. A feature of the invention is that it does not rely on direct tracking of edges, distance transforms, or wavelet analysis methods, but instead relies on analyzing Hough transform data. A benefit of the system is that it can be used to directly detect which edge is a continuous fiber edge without giving undue weight to shorter or longer edges.

A further object of the invention is to optimally match detected edges and lines as parallel lines. A feature of the system is that it optimally matches detected possible edges of the nanofibers, assigning two edges per nanofiber. A benefit of the system is that it efficiently matches up different edges to define actual fibers.

An additional object of the invention is to accurately detect nanofibers and other structures in an image. A feature of the invention is that its steps process input images to resolve nanofibers in any orientation. A benefit of the invention is that images and samples do not require pre-processing or manual review.

A further object of the invention is to reliably detect the diameters of the nanofibers. A feature of the invention is that the scale of the image is detected and saved and subsequently used to provide real-world measurements of the fibers in the image. A benefit of the invention is that it provides automatic detection of fiber diameters.

An additional object of the invention is the facilitation of machine learning and user input. A feature of the invention is that in one embodiment, the work product generated by the intermediate steps of the system are visualized and displayed to the operator to assist the automated processes. A benefit of the invention is that it can process images with operator assistance where needed, and can provide assurance to the operator that fibers were correctly detected.

A system for detecting features within an image is described which uses the following steps reading an input image file; preprocessing the input image file preserving scale information; detecting boundaries of features within the input image file generating boundary information data set; converting the boundary information data set using a Hough transform resulting in a Hough space data set; matching local maxima within the Hough space set; and outputting features matching the Hough space set.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

Figure 1:
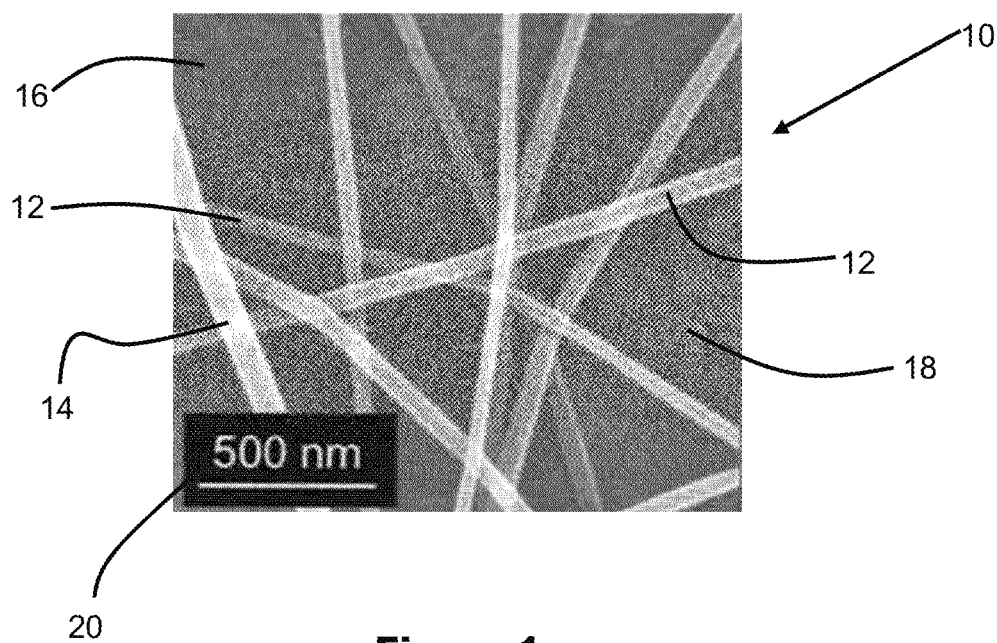
FIG. 1 depicts a sample image for analysis as used in one embodiment of the invention.

The foregoing summary, as well as the following detailed description of certain embodiments of the present invention, will be better understood when read in conjunction with the appended drawings.

To the extent that the figures illustrate diagrams of the functional blocks of various embodiments, the functional blocks are not necessarily indicative of the division between hardware circuitry. Thus, for example, one or more of the functional blocks (e.g. processors or memories) may be implemented in a single piece of hardware (e.g. a general purpose signal processor or a block of random access memory, hard disk or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Turning to the figures, FIG. 1 depicts a sample image 10. The sample image 10 as originally provided to the system is in color and is presented in dithered black and white for purposes of this filing.

The sample image 10 depicts one or more fibers 12 having varying dimensions and alignments. As shown in the figure, several of the fibers 12 are in the foreground, while other fibers 12 are partially obscured. The fibers 12 create intersection points 14 and sit against a background 16. The background 16 also includes non-fiber features 18 which could be dirt, imaging anomalies, and other input difficulties that should not be detected as actual fibers. The image also includes scale information 20. Input images also include other information, such as date and time or other identifying information (not depicted).

In one embodiment, the purpose of the invented system is to detect the number of fibers 12 in the image as well as their alignment, any points of overlapping, and other image features. Each continuous fiber 12, in one embodiment, is detected as a single unit, even when the fiber 12 overlaps other fibers, includes curved portions, and is partially obscured, in one embodiment. One embodiment of the invention accepts input images, such as sample image 10, without pre-processing and intervention.

Figure 2:
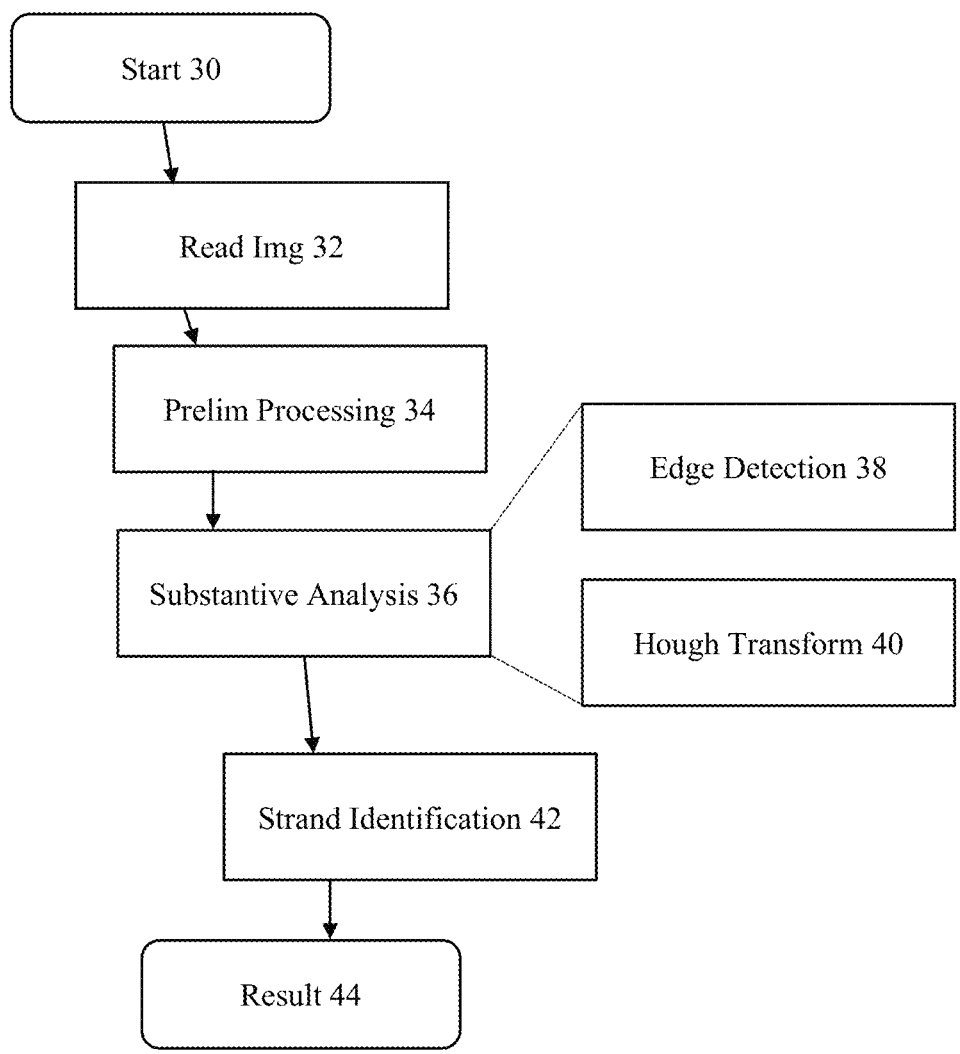
FIG. 2 depicts a flow chart of the processing steps of one embodiment of the invention.

An overview flowchart of the method is presented in FIG. 2. The analysis process 30 is shown as having discrete steps in FIG. 2. However, the analysis process 30 steps can occur in non-consecutive order with batch processing of input images and concurrent steps, implemented in one embodiment.

In one embodiment, the analysis process 30 operates on a single workstation or other multipurpose computer. The workstation comprises one or more storage devices, operating memory, processor, and an input/output bus. The system output and transformation steps performed by the system are described below. In another embodiment, the analysis process 30 operates using multiple processing units, both within a single workstation and by using multiple workstations or virtual machines. One embodiment of the analysis process 30 employs a single commercial-grade laptop, using the laptop hard drive as the primary storage device, the laptop's memory as the operating memory, the laptop CPU as the processor, and the laptop's input and output devices such as the keyboard, network connection, and physical display.

The analytical process 30 begins with reading of an input image 32, such as the sample image 10 shown in FIG. 1. In one embodiment, the reading of an input image 32 requires the user to provide a graphics file, such as a jpg image, or another image file format. The image file provided to the reading of an input image 32 step was obtained from an SEM or analogous equipment, in one embodiment.

In another embodiment, the reading of an input image 32 step occurs by the analysis process 30 querying a data source for the next image to process. In this embodiment, the analysis process 30 is automated to process all images from a specified data source.

In yet another embodiment, the reading of an input image 32 step comprises the analysis process 30 requesting a scan directly from an SEM or other test equipment. In this embodiment, the analysis process 30 is integrated into a test or analysis process of a manufacturing plant, such as an assembly line producing nanofiber materials. The analysis process 30, in this embodiment, selects time intervals during which to scan the output of the manufacturing process to determine whether quality criteria are met.

In yet another embodiment, the reading of an input image 32 step captures a video stream of the product subject to testing and converts the video stream into a series of input images.

The output of the reading of an input image 32 process is a multi-dimensional matrix of color values for each element of the input image. In one embodiment, the matrix assigns a value of 0 to 255 (or 8 bits) to each red, green, and blue components of the image, along with an alpha modifier. In this embodiment, the elements of the input image correspond to pixels. One embodiment has been tested with images of size 1146880 to 1228800 pixels, although the computational requirements allow images with as detailed a resolution as is commonly possible with SEM output.

Once the reading of the input image 32 is completed for an image, the analysis process 30 proceeds to the preliminary image processing step 34.

Following the preliminary image processing step 34, the image is ready for substantive analysis steps 36. In one embodiment, the first substantive analysis step 38 is edge detection.

Following the edge detection 38 step, the various edges within the image must be categorized. The second substantive analysis step 36 is the Hough transform step 40 using the output of the edge detection 38 data. The Hough transform step 40 results in the edge data being represented using Hough transform coordinates in polar space.

The output of the Hough transform step 40 is analyzed to identify the edges that comprise individual strands during the strand identification step 42. The analysis result 44 is an identification of individual strands, their diameters, and the discarding of non-strand elements in the input data.

Preliminary Image Processing

Figure 3:
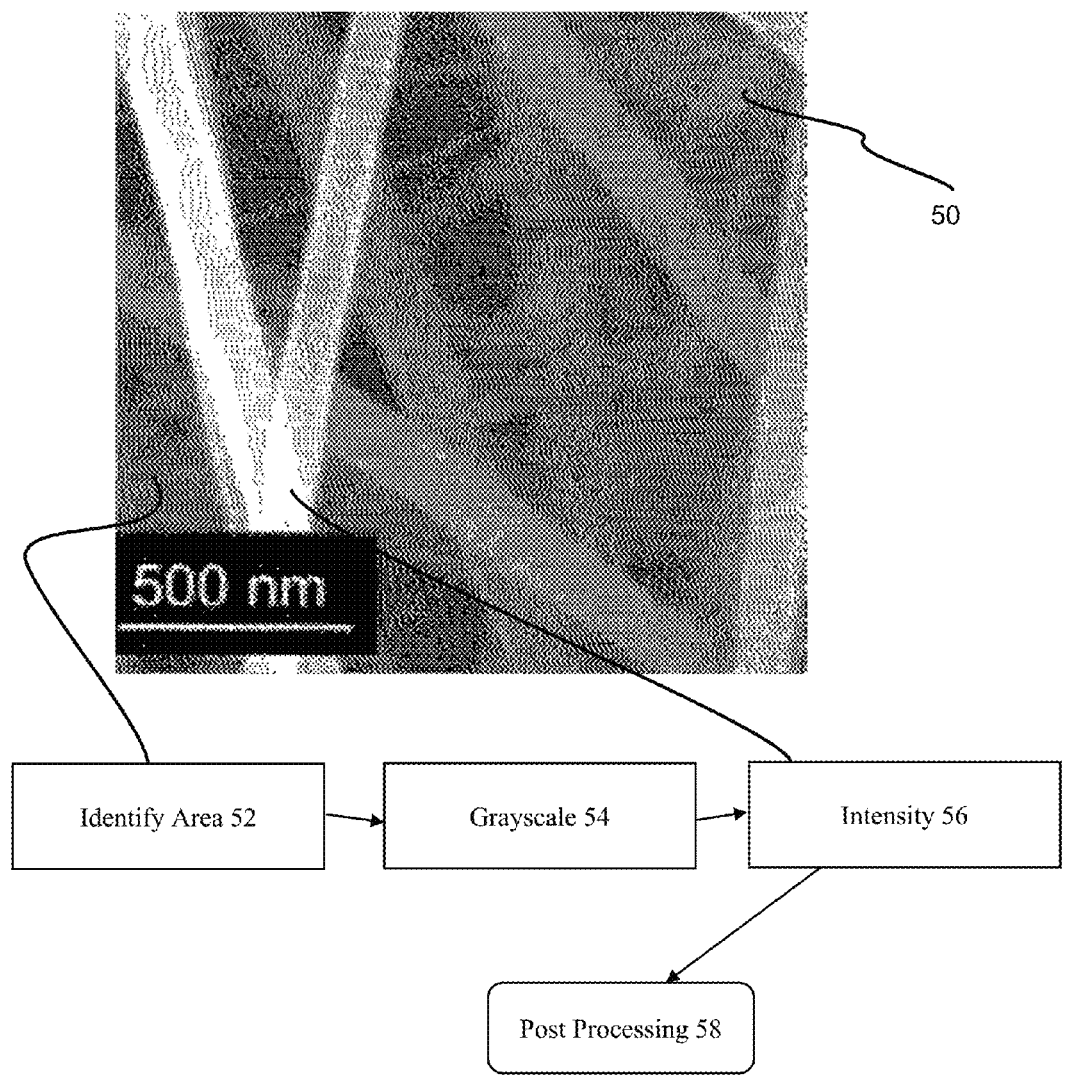
FIG. 3 depicts a flow chart of the preprocessing steps of one embodiment of the invention.

Turning to FIG. 3, the details of the preliminary image processing step 34 are depicted therein, for one embodiment of the invention.

The preliminary image processing step 34 accepts as input an input image 50, which has been read into system memory during the reading of an input image step 32. In one embodiment, the image processing step 34 accepts the 24-bit color scanning microscope image as the input image 50.

The first step for the preliminary processing step 34 is to crop unnecessary information to create a relevant operational area 52 for the input image 50. In one embodiment, the crop area is focused on labels such as the scale, and any information at the bottom of the image, such as microscope identifying information, and other text that could interfere with the subsequent analysis. Inasmuch as the scale and text appears on a black-background rectangle, in one embodiment, the crop algorithm examines the input image 50 for black rectangles, which are defined as areas where the R, G, and B values are all 0. In one embodiment, the scale information of the image 50, while cropped out, is preserved separately from the image 50, to assist in the calculation of the final diameter value of each strand.

In one embodiment, following the identification of the relevant operation area 52 of the image 50, the area 52 is converted to a grayscale image 54. In one embodiment, the conversion occurs by colorimetric conversion to grayscale, by assigning each color a weight constant and adding the contributions of each component to form a grayscale value. In one embodiment, the constants used are 0.2989 for the red value, 0.5870 for the green value, and 0.1140 for the blue value.

The grayscale conversion is subject to an intensity cutoff analysis 56, in one embodiment. The grayscale image 54 contains values for each pixel, and those above a certain intensity cutoff value 56 are set to the intensity cutoff value 56. The pixels below the intensity cutoff value 56 are unchanged during this step. In one embodiment, the intensity cutoff value 56 is set to 176 (wherein the values range from 0 to 255), which prevents excessively bright areas in the image 54 from creating artificial edges within a single strand caused by intensity gradients within a single strand. The setting of the cutoff value 56 is user-selectable, in one embodiment.

In one embodiment, if the intensity cutoff value 56 results in changes to more than a majority of the pixels the input image 50 is rejected as having too low quality. In another embodiment, the system generates a warning about the image quality if there are too many pixels that have been subject to the intensity cutoff process 56.

The output of the preliminary image processing step 34 is a cropped grayscale image having no overly bright areas. This post-processing image 58 is used as input for subsequent steps.

If any of the steps of the preliminary image processing step 34 fail, the system generates an appropriate notification on the output system. For example, if there does not appear to be any scale information within the input image 50, the user is asked to select a manual scale, or a default scale value is used for the type of SEM identified in the metadata of the image file 50.

Edge Detection

Figure 4:
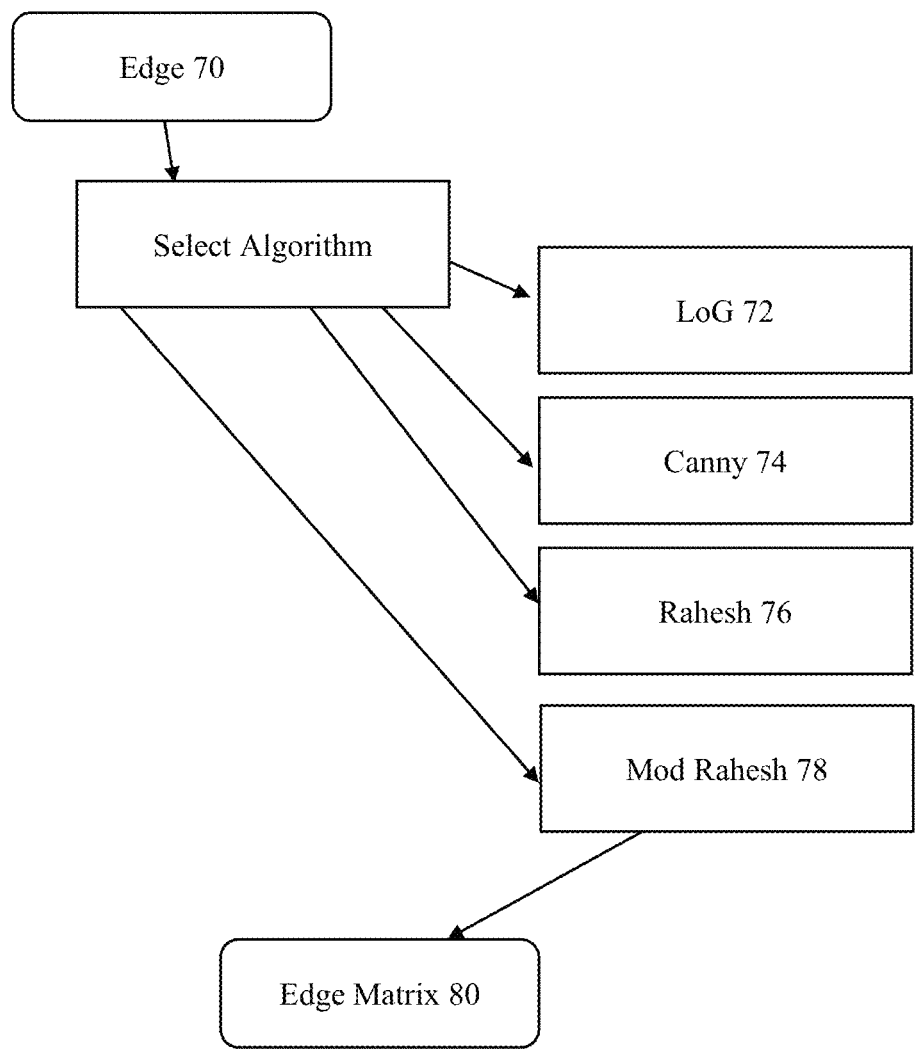
FIG. 4 depicts a flow chart of the edge detection steps of one embodiment of the invention.

The post-processing image is thereafter subject to the edge detection step, detailed in FIG. 4 for one embodiment of the system.

The edge detection, as used in one embodiment, does not require a particular intensity differential between the fibers and the background. In one post-processing image 58 the fibers will be darker than a background. In another post-processing image 58 the fibers are lighter than a background. In use of one embodiment, wetted fibers within the post-processing image 58 are particularly difficult to analyze as their relative intensity to the background changes depending on the level of moisture in the fiber at the time of the generation of the original image 50.

Measurements of nanotube characteristics, such as inside and outside diameter, is implemented with a similar methodology discussed for partially wetted nanofibers, in one embodiment. Applications of this technology include quantifying extent and yield of carbon nanotubes functionalized by peptides or other chemical agents for particular bioengineering applications by automatically characterizing TEM images.

In one embodiment, the post-processing image 58 is submitted to an edge detection algorithm selector 70. In one embodiment, three different algorithms are used to detect edges within the post-processing image 58. In another embodiment, the selector defaults to only one algorithm, unless the algorithm is unable to detect the expected number of edges within the image.

One algorithm is the Laplacian of Gaussian algorithm (LoG) 72 wherein the post-processing image is subject to iterative steps of Gaussian blurring prior to applying feature detection. In one embodiment, the LoG parameters are threshold value of 1.63e-4, and Gaussian sigma=5.

A second possible algorithm is the Canny algorithm 74. In this embodiment, the Canny parameters are threshold1=0.116, threshold2=0.289, and sigma=2.8. A third algorithm is the Rakesh local thresholding algorithm 76.

In one embodiment, several modifications to the Rakesh local thresholding algorithm 76 are used resulting in a modified Rakesh edge detection algorithm 78. The primary modification in one embodiment, is the use of a local neighborhood smaller than the total image for performing standardized gradient magnitude statistics, denoted by S(x, y), equation 10 in the Rakesh paper, reproduced below:

$$S(x, y) = \frac{f_x^2 \sigma_{22}(x, y) + f_y^2 \sigma_{11}(x, y) - 2\sigma_{12}(x, y) f_x f_y}{\sigma_{11}(x, y) \sigma_{22}(x, y) - \sigma_{12}^2(x, y)}$$

The conventional Rakesh algorithm calculates the statistical value S accounting for every other pixel in the image for each pixel location (x,y), where in the modified algorithm used by one embodiment of the invention, the analysis is defined in a local neighborhood and only look at that neighborhood when calculated the S(x,y) metric, in the current embodiment. In one embodiment, the local neighborhood size used was 50 by 50 pixels.

A further modification in the instant embodiment, was special treatment of pixels close to the border of the image; the most extreme pixels are ignored (cannot be edge pixels), and the pixels within a threshold value of the border (such as 25 pixels from the border) have a neighborhood including the first 50 pixels in that dimension. In this embodiment, the pixel is not necessarily in the middle of the local region tested. Inasmuch as strands approach the border, the instant embodiment includes the border values in the analysis, and the Rakesh paper does not explain how they handle these border issues. A further modification is to not use a smoothing parameter (h=1). In one embodiment, the two threshold values S1 and S2 used for experiments are 3.4 and 11.9.

The final output is an edge matrix 80 containing edge data, which indicates which pixels, are on edges, and which pixels do not comprise edges. In one embodiment, each pixel is assigned only a binary value. In another embodiment, pixels are assigned more than one designation, such as in Canny's algorithm where pixels are classified as non-edge, 'major' edge and 'minor' edge. Major edges are automatically actual edges, but minor edges are only actual edges if the edge continues to be part of an edge formed by major edges. This embodiment is referred to as "thresholding with hysteresis" and is a primary innovation of Canny's algorithm.

The edge matrix 80 is used as input for the Hough transform step to detect individual lines within the edge matrix 80.

Hough Transform

Figure 5:
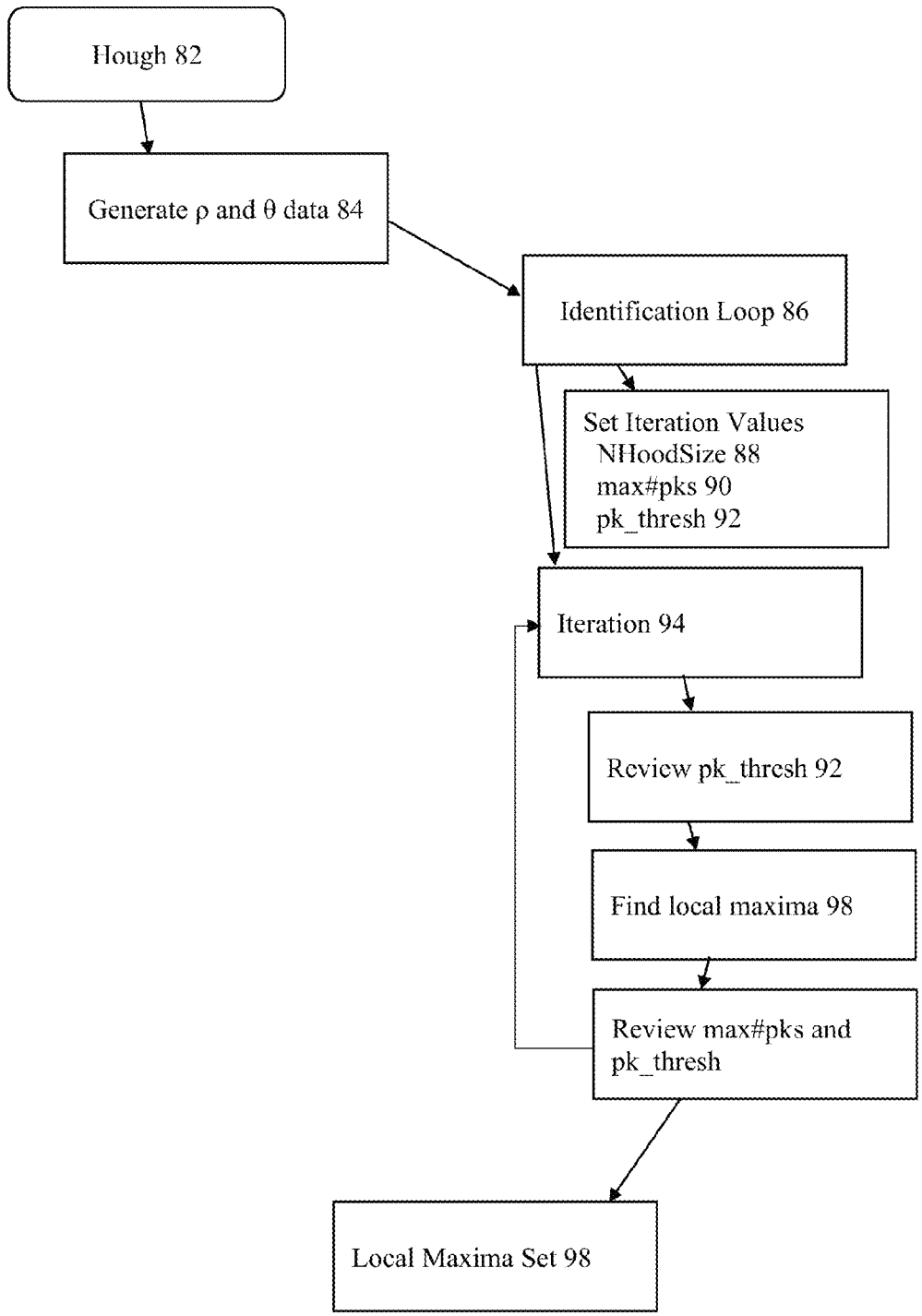
FIG. 5 depicts the Hough transform steps of one embodiment of the invention.

The Hough transform step 40, one embodiment of which is shown in FIG. 5, is designed to identify which edges from the edge matrix 80 define continuous lines. For each line represented within the edge matrix 80, a pair of points $\rho$ and $\theta$ are defined in polar coordinates. As such, the outputs 82 of the Hough transform step 40 are two arrays or vertices of $\rho$ and $\theta$ data 84.

In one embodiment, the Hough transform assigns a maximum value to straight and continuous lines, and optimum nanofibers define straight and continuous segments. Nonetheless, as the strands are not optimum in most circumstances, and because the edge matrix 80 does not contain values that represent true edges, the Hough transform will likewise contain more than one high value for a single line or fiber edge. The process of identifying each strand 86 therefore ensures that only one maximum value is selected for each strand edge.

The identification step 86 requires an iterative loop which factors several parameters to determine which segment comprises a true fiber edge, and which is an undesired edge such as bead edges or textures in the background.

In one embodiment, the iterative loop relies on two limiting values, NHoodSize 88, max#pks 90, and several iterative calculation values pk_thresh 92, pk_thresh_int 94 and a counter of the steps pk_thresh_step 96.

NHoodSize 88 is the minimum distance between local maxima in the Hough space 82. A local maximum in Hough space 82 defines a line. NHoodSize 88 prevents the finding of two lines in immediate proximity, as would happen if a bead edge was detected as a different fiber edge. However, NHoodSize 88 cannot be set too high, as doing so would prevent two parallel lines from being detected as two separate lines. As such, NHoodSize 88 is set to [33,3], representing [$\rho$, $\theta$], where rho_resolution=theta_resolution=0.5 pixels (so NHoodSize=66 and 6 pixels for $\rho$ and $\theta$ respectively) in one embodiment.

The parameter max#pks 90 is a counter for the maximum number of local maxima that can be found, with each local maxima representing a line. In one embodiment, the value is set to 250 as the input image is unlikely to contain more than 125 fibers or half the max#pks 90 value. The value accounts for the fact that more than one set of Hough peaks can describe the same fiber (as occurs when a fiber includes a bend), and so the number of fibers recognized will be less than the number of Hough peaks found, in majority of cases.

In one embodiment, the parameter pk_thresh 92 is the minimum score allowed for a local maxima to be considered, which again avoids overly short segments, as would occur with beads on a straight segment. In one embodiment, the pk_thresh 92 is a function of the highest Hough score within the Hough space 82 of the image.

The iteration step 94 begins by setting pk_thresh 92 to a predefined pk_thresh_int 94. In one embodiment, pk_thresh_int 94 is set to 0.2. In another embodiment pk_thresh_int 94 is a function of the input Hough space 82. The maximum score of the Hough space 82 is recorded as max_score.

During the iteration, each successively lower local maxima is recorded until max#pks value is reached, or if there are no more scores greater than pk_thresh*max_score. The iterative process ends if this occurs.

However, if the max#pks value is reached without using low values, the process is repeated except pk_thresh is incremented by pk_thresh_step. As such, with each step, the only comparison is the finding of local maxima within the Hough space 82.

The iterative process improves one embodiment of the invention by facilitating finding peaks in both high density and low density areas, so long as the same max_score value can be used.

The final output of the iterative process is the identification of local maxima 98, with each maximum in Hough space 82 representing one straight line segment.

Another embodiment incorporates a circular Hough transform in place of linear Hough transform. This circular Hough transform provides a method to characterize SEM and TEM images of nanoparticles, and not simply nanofibers. In this embodiment, the system is able to quantify size, polydispersity, and shape of the particles. This method is sensitive to small size increases from surface-functionalization of nanoparticles for medical imaging (magnetic nanoparticles) or improving cell uptake (lipid nanoparticles). Other methods of nanoparticle characterization such as dynamic light scattering (DLS) or NanoSight have limitations in detecting small nanoparticle size differences that are clear SEM or TEM images.

Strand Identification

Figure 6:
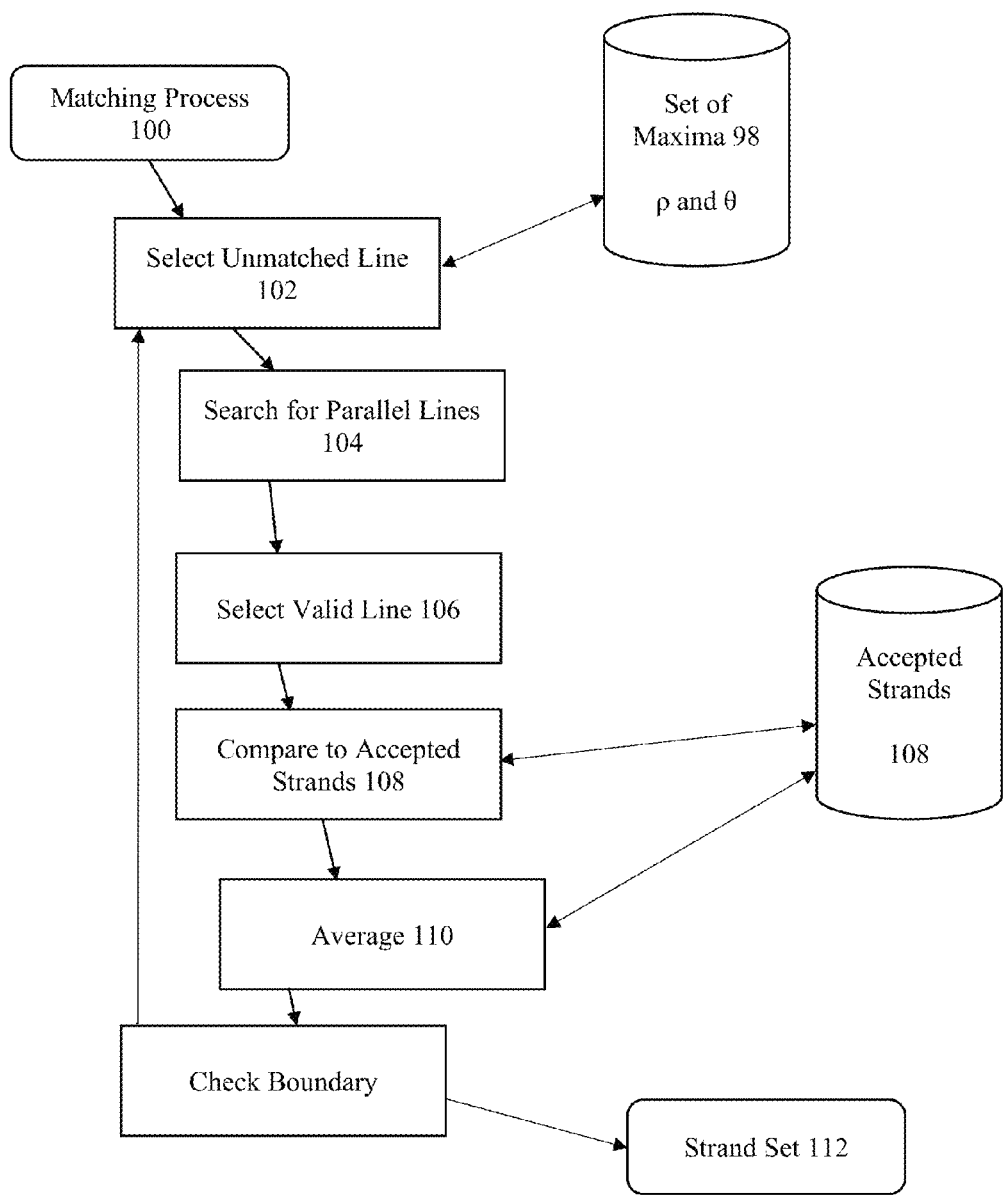
FIG. 6 depicts the matching steps of one embodiment of the invention.

Following the identification of local maxima, the line segments in the Hough space 82 are identified. Identification of strands per one embodiment is described in FIG. 6.

The process of strand identification matches the line segments to one another. Each line segment, having been identified in the prior step, has a $\rho$ and $\theta$ data value 84.

The distance in normal space is defined as the absolute value of the difference between the $\rho$ values of each line or local maxima in Hough space 82. Inasmuch strands are defined by parallel lines, and parallel lines have the same $\theta$ data 84 value, the primary problem is grouping actual fibers and not distant lines. As such, in one embodiment, maximum θ data 84 differences between the parallel lines is used. In one embodiment, the chosen values are a function of user input, in another embodiment, the maximum and minimum values are the expected number of pixels for a real expected fiber given the magnification level of the image 50.

In one embodiment, the matching process 100 selects an unmatched line 102 and finds all other unmatched lines that are parallel to the selected line 102. If there exists at least one parallel line 104, the selected line 102 will be matched to it only if it is a valid parallel line. The process for checking whether a pair of lines defines a valid set 106 comprises initially matching to the parallel line 104 having the minimum distance between the lines. If the initial match is within the allowed size parameters, the selected line and the parallel line 104 are considered a valid strand candidate 106. The valid strand candidate 106 is compared to the current accepted candidates 108, if any. If the valid candidate 106 is similar to another current accepted candidate 108, then the average 110 of the valid candidate and the other current accepted candidate 108 becomes the new entry in the current accepted candidate 108. In one embodiment, a set is considered similar to a pre-existing set if the locations of the maxima within the image are within a threshold distance to an existing maximum. At the end of the matching algorithm, each set that has more than one pair in the set of similar maxima have the diameter measurements and theta values averaged over all similar maxima matches. For Hough maxima pairs without other similar pairs, no averaging is necessary. In one embodiment, the thresholds used to define similar pairs are 40 and 10 for ρ and θ respectively.

If a match is successful then the lines are removed from the unmatched line set and the process continues until there are no more potential unmatched lines.

The algorithm is robust in that it can detect curved long fibers as a single fiber, as what occurs with the calculation of the average 110 strand from a new potential candidate strand 106 and the set of existing strands.

The final output is the set of strands 112 found within the image, with the longest to the shortest continuous strands represented.

Computational Complexity

The system as described herein offers a known upper bound on the number of calculations needed to complete each step. For example, given a sample image having n×m pixels, the limits are, as expressed using "Big O" limits:

Reading of an input image step 32—O(n*m)

Preprocessing of the input image step 34—O(n*m)

Edge detection step 38—O(n*m), with varying effectiveness of the chosen algorithms, including Canny, which is O(m*n*log(m*n)).

Hough peaks is i*O(p$^3$), where p=number of edge pixels, and i is the iteration value of the algorithm, with more repetitions if max#pks is exceeded (and again if exceed again). In one embodiment, if max#pks is exceeded 3 times (for example), the entire system will take almost 3 times as long to complete as if #pks <250 on the first iteration of the algorithm.

Hough peak matching is O(n$^2$) where n=number of pks (<=250)

Bend-detect is O(n$^2$) where n=number of pk matches (<=125)

A further benefit is that multiple steps can occur concurrently, especially when processing a batch set of images.

Example Output

Figure 7:
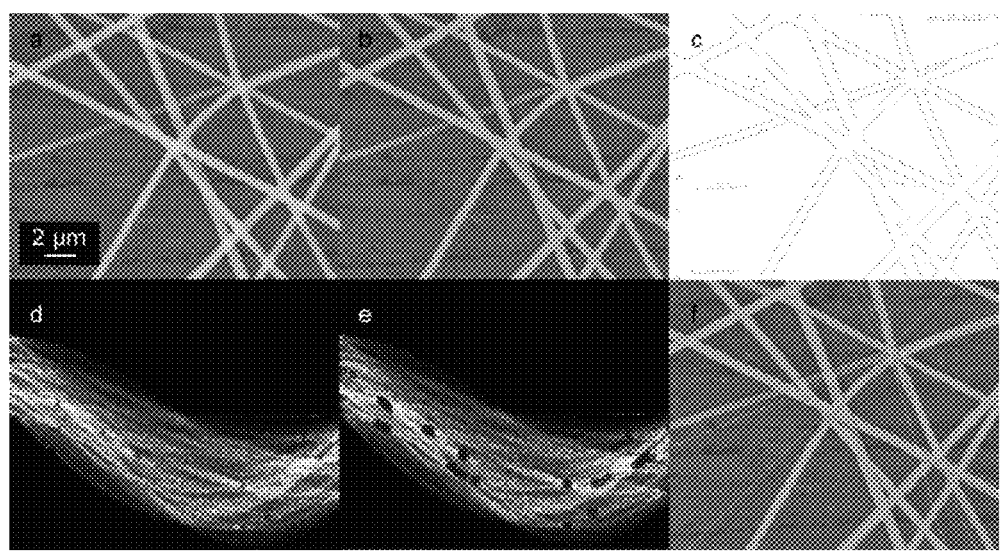
FIGS. 7A-F depict images of the steps of the invention according to one embodiment.

As depicted in FIG. 7A-F, the output of each step is shown for one image in one embodiment. Shown in FIG. 7A, a sample image has been read into the system. The sample image includes scale information. In FIG. 7B, the sample image has undergone pre-processing while FIG. 7C shows a visualization of the output of the edge detection process. FIG. 7D depicts the image following Hough analysis and FIG. 7E highlights the local maxima. Finally 7F shows the paired local maxima, superimposed over the original image, which represent each fiber.

Assisted Process

While the processes of one embodiment of the invention operate sequentially and without user intervention, in one embodiment, a user is presented confirmation screens at several sub-steps and asked to provide feedback. For example, the user may be asked to confirm that the edge detection has correctly identified all of the strand edges or if a different algorithm should be attempted. In another embodiment, the user is asked to confirm that the matching of edges is correct, especially if there are many unmatched edges or if the diameters of the matched edges approach or exceed a threshold value.

In another embodiment, the output of the system is compared to selected manual counting and manual identification of strands performed on only a sample of total inputs. In this embodiment, the type of edge detection used is optimized to decrease the error rate.

Figure 8:
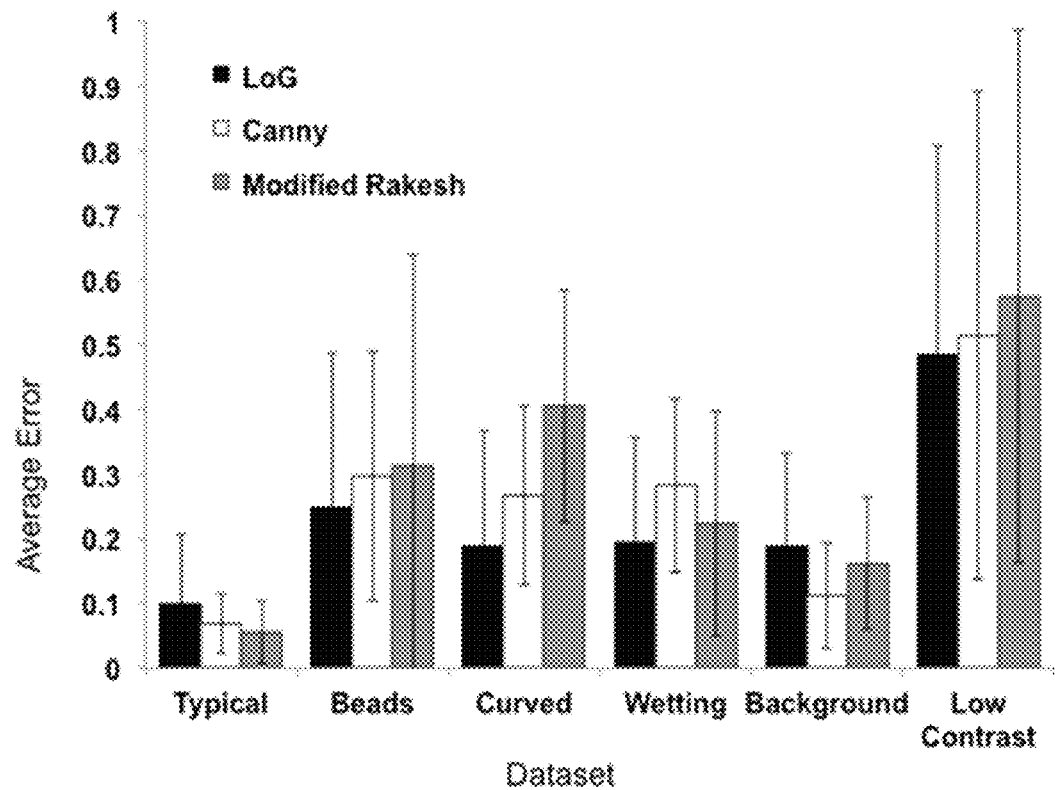
FIG. 8 depict the results and error values of various algorithms implemented in one embodiment of the invention.

As can be seen from the chart in FIG. 8 the error rates for each algorithm vary depending on the type of problem with the input file. For example, as shown in FIG. 8, low contrast images have the higher error rate. The error rate as depicted in FIG. 8 is described as follows:

$$\text{Error} = \left| \frac{\overline{D_{IJ}} - \overline{D_s}}{\overline{D_{IJ}}} \right|$$

where $\overline{D_{IJ}}$ is the manual measured mean diameter of an image from a given input file Image$_J$ and $\overline{D_s}$ is the automatic system measurement.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The invention claimed is:

1. A system for detecting features within an image comprising:
   a) reading an input image file;
   b) preprocessing the input image file preserving scale information;
   c) detecting boundaries of features within the input image file generating boundary information data set;
   d) converting the boundary information data set using a Hough transform resulting in a Hough space data set;
   e) matching local maxima within the Hough space set;
   f) outputting features matching the Hough space set; and
   g) calculating distance values of possible strands from the Hough space data set and selecting the closest parallel edges as potential lines.

2. The system for detecting features within an image of claim 1 where said features comprise strands.

3. The system for detecting features within an image of claim 2 wherein said boundary information comprises edges of individual strands.

4. The system for detecting features within an image of claim 1 wherein detecting boundaries uses a laplacian of Gaussian algorithm.

5. The system for detecting features within an image of claim 1 wherein detecting boundaries uses a thresholding with hysteresis algorithm.

6. The system for detecting features within an image of claim 1 wherein detecting boundaries comprises detecting edges by thresholding a gradient using statistical principles.

7. The system for detecting features within an image of claim 6 wherein said detecting boundaries algorithm is operated on subparts of the image.

8. The system for detecting features within an image of claim 1 wherein output of each step is presented to an end user.

9. The system for detecting features within an image of claim 8 wherein output of the detecting boundaries step is presented to the end user and the end user is asked to confirm that edges were correctly identified.

10. The system for detecting features within an image of claim 1 wherein said input file depicts wetted fibers.

11. The system for detecting features within an image of claim 1 wherein said input image comprises nanoparticles.

12. The system for detecting features within an image of claim 11 wherein said Hough space data set comprises detection of circular features.

* * * * *